(12) United States Patent
Yoon et al.

(10) Patent No.: US 6,261,307 B1
(45) Date of Patent: Jul. 17, 2001

(54) METHOD OF USING SURGICAL INSTRUMENT WITH ROTATABLY MOUNTED OFFSET END EFFECTOR

(76) Inventors: InBae Yoon, 2101 Highland Ridge Dr., Phoenix, MD (US) 21131; Samuel C. Yoon, 719 Leister Dr., Timonium, MD (US) 21093

( * ) Notice: Subject to any disclaimer, the term of this patent is extended or adjusted under 35 U.S.C. 154(b) by 0 days.

(21) Appl. No.: 09/564,789

(22) Filed: May 5, 2000

Related U.S. Application Data

(62) Division of application No. 08/847,252, filed on May 1, 1997, now Pat. No. 6,080,180.

(51) Int. Cl.$^7$ .................................................. A61B 17/28
(52) U.S. Cl. .............................. 606/205; 606/1; 600/201; 600/101
(58) Field of Search .................................. 606/1, 53, 79, 606/110, 113, 119, 138, 139, 140, 142, 144, 145, 146, 148, 167, 170, 205–211; 600/201, 204, 206, 101, 104, 138, 153, 156, 160, 178, 182; 81/300

(56) References Cited

U.S. PATENT DOCUMENTS

| | | |
|---|---|---|
| 919,138 | 4/1909 | Drake et al. . |
| 1,037,864 | 9/1912 | Carlson et al. . |
| 1,131,163 | 3/1915 | Saunders et al. . |
| 1,155,378 | 10/1915 | Steedman . |
| 1,449,087 | 3/1923 | Bugbee . |
| 1,822,330 | 9/1931 | Ainslie . |
| 2,213,830 | 9/1940 | Anastasi . |
| 2,580,964 | 1/1952 | Skaller . |
| 2,601,564 | 6/1952 | Smith . |
| 2,646,045 | 7/1953 | Priestley . |
| 2,959,172 | 11/1960 | Held . |
| 3,090,386 | 5/1963 | Curtis . |
| 3,139,089 | 6/1964 | Schwerin . |
| 3,349,772 | 10/1967 | Rygg . |
| 3,470,875 | 10/1969 | Johnson . |
| 3,842,840 | 10/1974 | Schweizer . |
| 3,946,740 | 3/1976 | Bassett . |
| 4,109,658 | 8/1978 | Hughes . |
| 4,164,225 | 8/1979 | Johnson et al. . |
| 4,257,420 | 3/1981 | Terayama . |
| 4,440,171 | 4/1984 | Nomoto et al. . |
| 4,557,265 | 12/1985 | Andersson . |
| 4,621,640 | 11/1986 | Mulhollan et al. . |
| 4,635,638 | 1/1987 | Weintraub et al. . |
| 4,935,027 | 6/1990 | Yoon . |
| 5,037,433 | 8/1991 | Wilk et al. . |
| 5,100,421 | 3/1992 | Christoudias . |
| 5,147,373 | 9/1992 | Ferzli . |
| 5,181,919 | 1/1993 | Bergman et al. . |
| 5,209,741 | 5/1993 | Spaeth . |
| 5,211,650 | 5/1993 | Noda . |
| 5,222,508 | 6/1993 | Contarini . |
| 5,234,443 | 8/1993 | Phan et al. . |

(List continued on next page.)

FOREIGN PATENT DOCUMENTS

| | | |
|---|---|---|
| 337579 | 4/1904 | (FR) . |
| 395073 | 8/1973 | (SU) . |

*Primary Examiner*—Glenn K. Dawson
(74) *Attorney, Agent, or Firm*—Blank Rome Comisky & McCauley LLP

(57) ABSTRACT

An instrument for operating on anatomical tissue includes a barrel having at least one shaft. An end is offset from the shaft. In an insertion position, the end effector is confined within the diametrical dimension of the barrel at a distal end thereof. After insertion, the end effector can be manipulated to extend beyond the diametrical dimension of the barrel to provide a large working span in which tissue can be manipulated.

7 Claims, 7 Drawing Sheets

U.S. PATENT DOCUMENTS

| | | |
|---|---|---|
| 5,244,948 | 9/1993 | Mulhaupt et al. . |
| 5,261,917 | 11/1993 | Hasson et al. . |
| 5,281,238 | 1/1994 | Chin et al. . |
| 5,304,185 | 4/1994 | Taylor . |
| 5,305,121 | 4/1994 | Moll . |
| 5,308,353 | 5/1994 | Beurrier . |
| 5,320,632 | 6/1994 | Heidmueller . |
| 5,336,230 | 8/1994 | Leichtling et al. . |
| 5,336,231 | 8/1994 | Adair . |
| 5,356,424 | 10/1994 | Buzerak et al. . |
| 5,364,408 | 11/1994 | Gordon . |
| 5,364,409 | 11/1994 | Kuwabara et al. . |
| 5,374,275 | 12/1994 | Bradley et al. . |
| 5,376,096 | 12/1994 | Foster . |
| 5,389,098 | 2/1995 | Tsuruta et al. . |
| 5,389,103 | 2/1995 | Melzer et al. . |
| 5,395,367 * | 3/1995 | Wilk .......................................... 606/1 |
| 5,397,325 | 3/1995 | Della Badia et al. . |
| 5,403,328 | 4/1995 | Shallman . |
| 5,403,329 | 4/1995 | Hinchcliffe . |
| 5,437,681 | 8/1995 | Meade et al. . |
| 5,454,823 | 10/1995 | Richardson et al. . |
| 5,462,561 | 10/1995 | Voda . |
| 5,462,562 | 10/1995 | Elkus . |
| 5,468,251 | 11/1995 | Buelna . |
| 5,470,338 | 11/1995 | Whitfield et al. . |
| 5,474,057 | 12/1995 | Makower et al. . |
| 5,474,568 | 12/1995 | Scott . |
| 5,477,794 | 12/1995 | Klundt . |
| 5,478,344 | 12/1995 | Stone et al. . |
| 5,478,345 | 12/1995 | Stone et al. . |
| 5,480,406 | 1/1996 | Nolan et al. . |
| 5,496,310 | 3/1996 | Exconde et al. . |
| 5,496,334 | 3/1996 | Klundt et al. . |
| 5,503,634 | 4/1996 | Christy . |
| 5,520,703 | 5/1996 | Essig et al. . |
| 5,540,704 | 7/1996 | Gordon et al. . |
| 5,540,705 | 7/1996 | Meade et al. . |
| 5,545,148 | 8/1996 | Wurster . |
| 5,562,640 | 10/1996 | McCabe et al. . |
| 5,562,685 | 10/1996 | Mollenauer et al. . |
| 5,562,686 | 10/1996 | Sauer et al. . |
| 5,562,703 | 10/1996 | Desai . |
| 5,569,164 | 10/1996 | Lurz . |
| 5,569,269 | 10/1996 | Hart et al. . |
| 5,569,270 | 10/1996 | Weng . |
| 5,573,542 | 11/1996 | Stevens . |
| 5,578,048 | 11/1996 | Pasqualucci et al. . |
| 5,582,617 | 12/1996 | Klieman et al. . |
| 5,591,181 | 1/1997 | Stone et al. . |
| 5,601,575 | 2/1997 | Maesamer et al. . |
| 5,603,718 | 2/1997 | Xu . |
| 5,607,435 | 3/1997 | Sachdeva et al. . |
| 5,609,601 | 3/1997 | Kolesa et al. . |
| 5,626,588 | 5/1997 | Sauer et al. . |
| 5,632,751 | 5/1997 | Piraka . |
| 5,632,752 | 5/1997 | Buelna . |
| 5,643,292 | 7/1997 | Hart . |
| 5,662,663 | 9/1997 | Shallman . |
| 5,674,230 | 10/1997 | Tovey et al. . |
| 5,702,407 | 12/1997 | Kaji . |
| 5,707,379 | 1/1998 | Fleenor et al. . |
| 5,709,693 | 1/1998 | Taylor . |
| 5,709,694 | 1/1998 | Greenberg et al. . |
| 5,713,908 | 2/1998 | Jameel et al. . |
| 5,722,990 * | 3/1998 | Sugarbaker et al. .................. 606/207 |

* cited by examiner

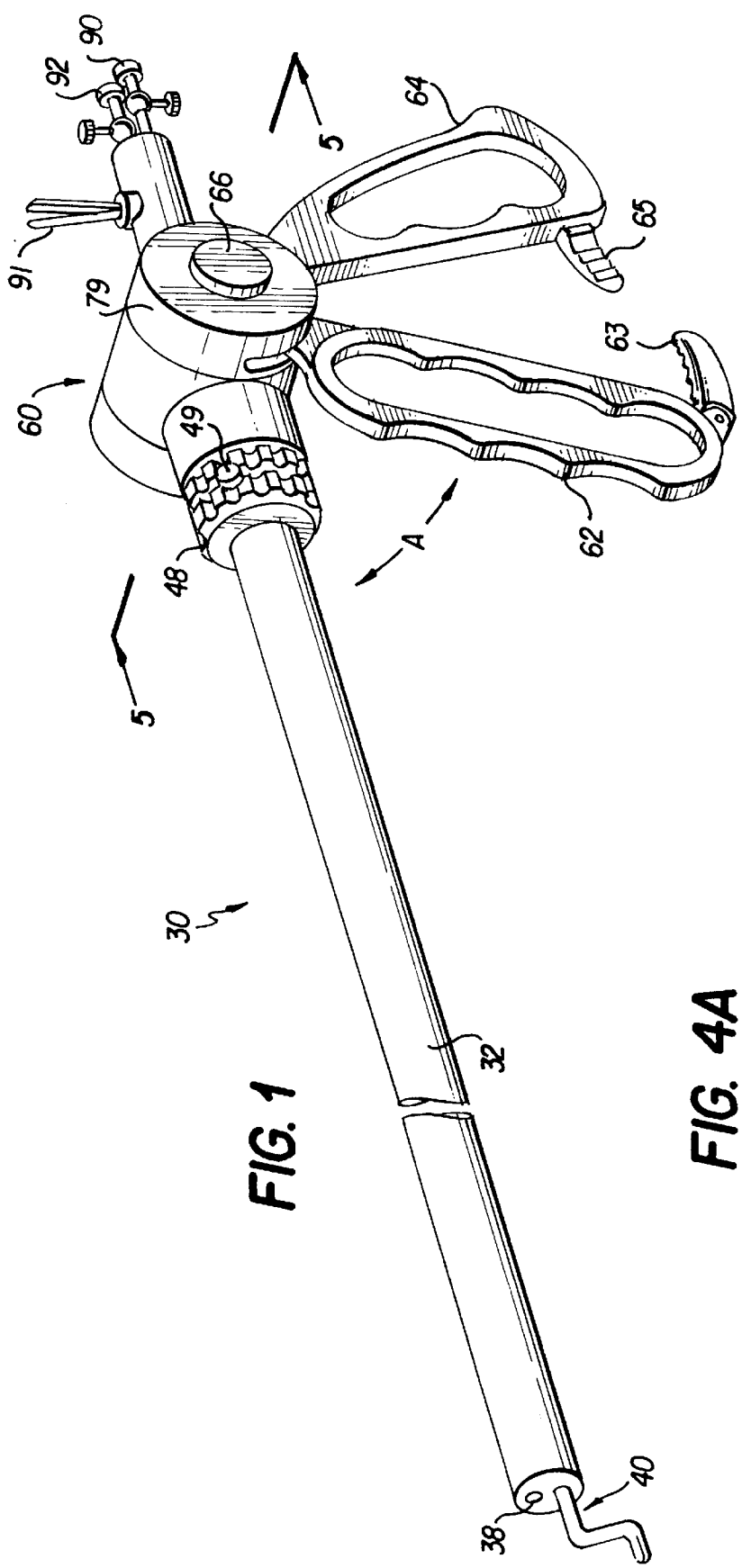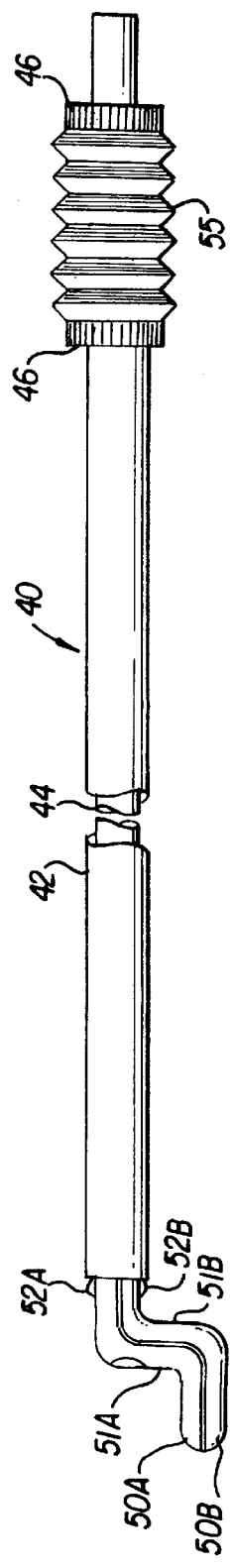

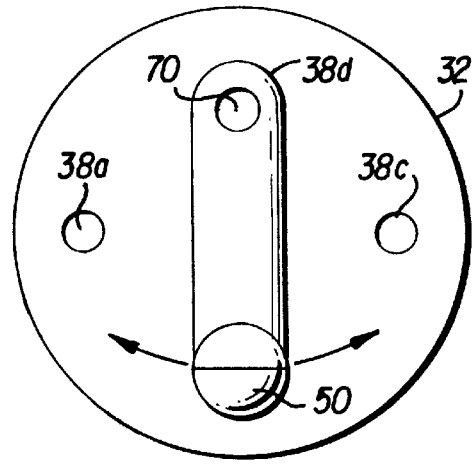
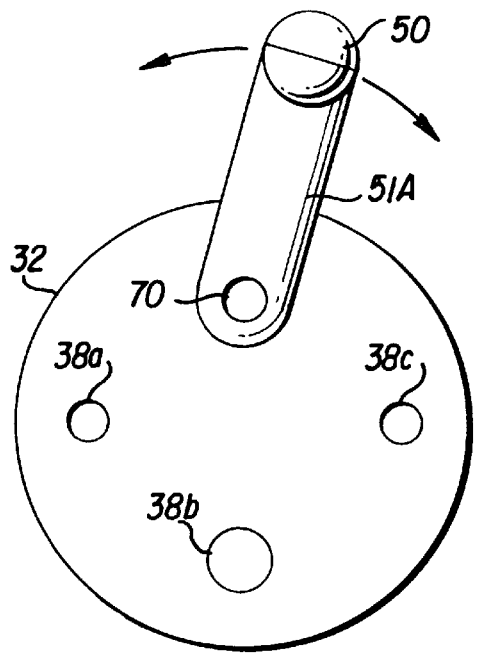
FIG. 2A  FIG. 2B
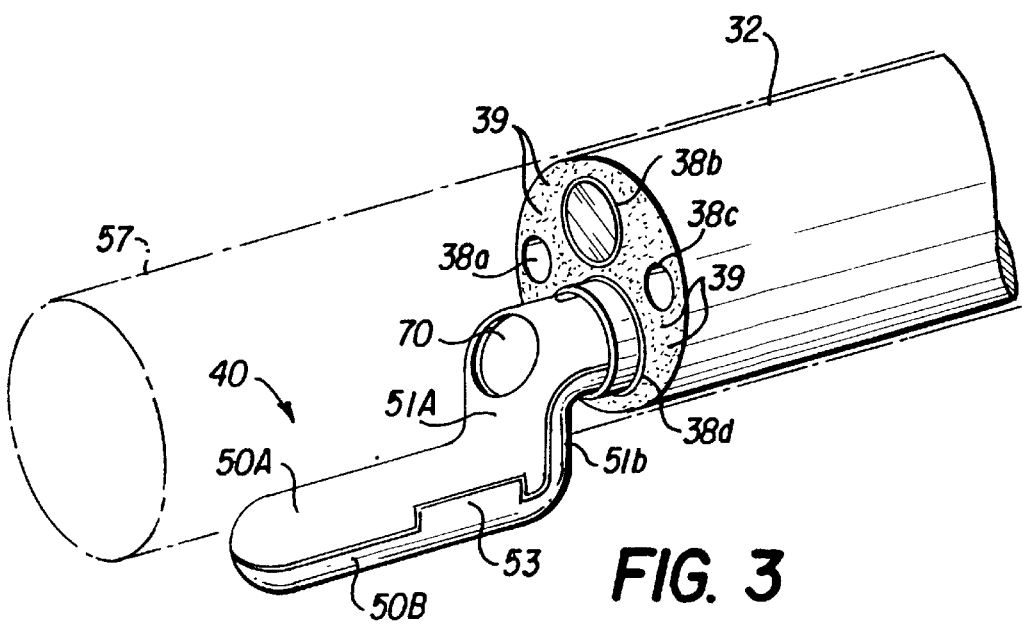
FIG. 3

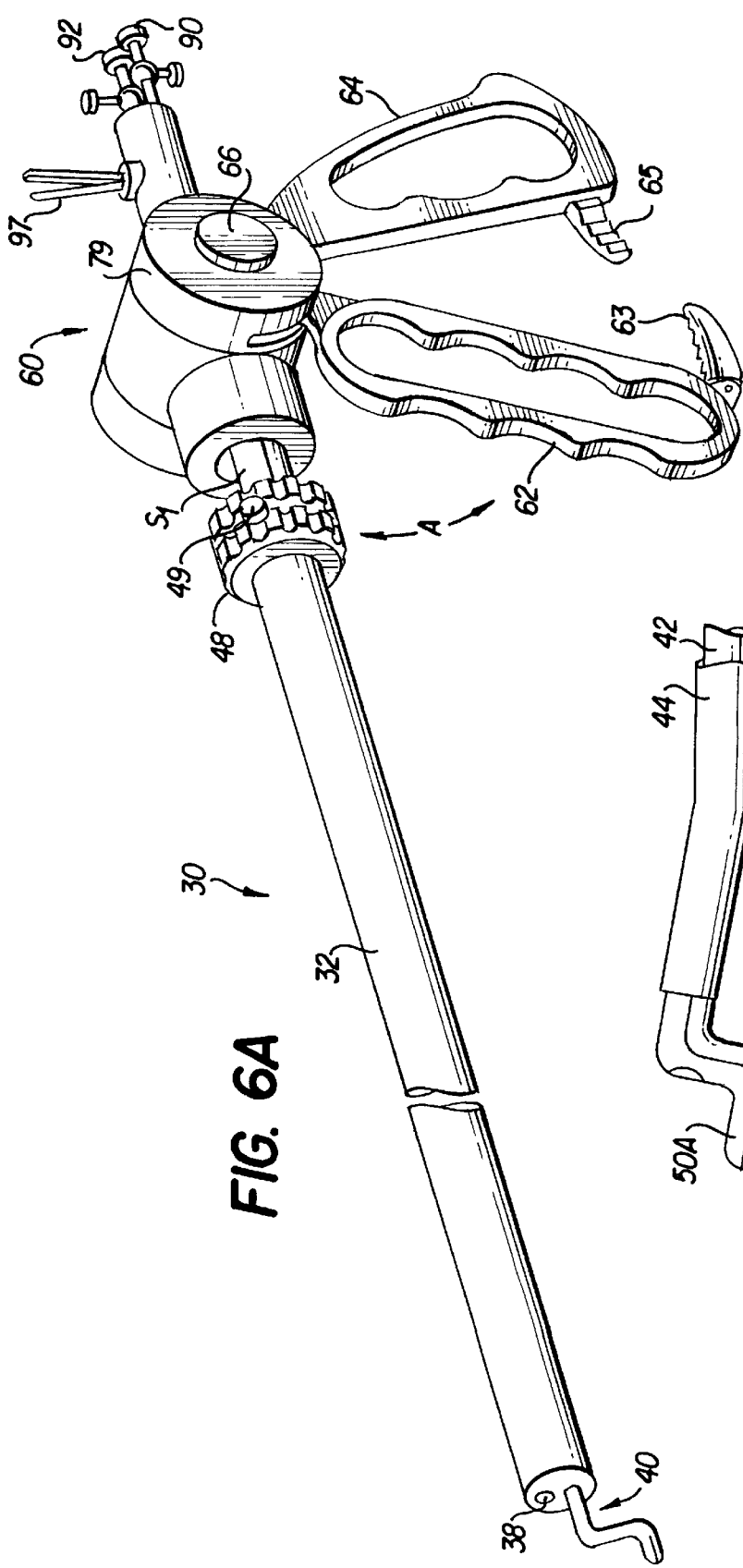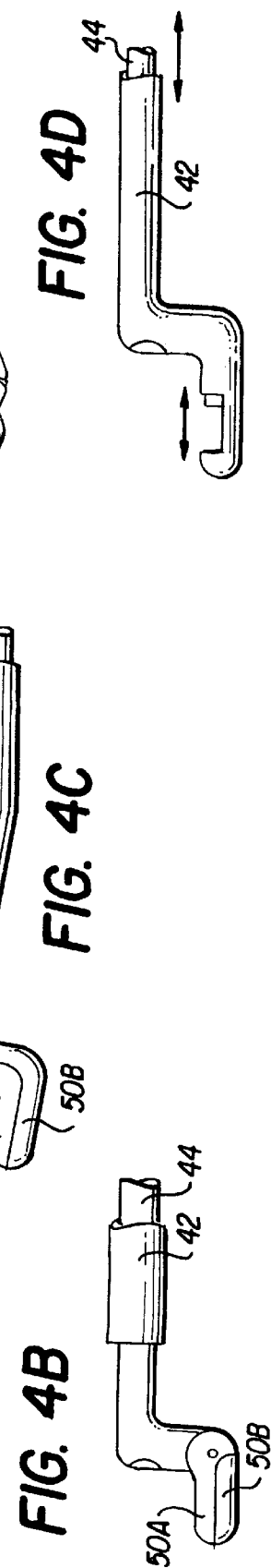

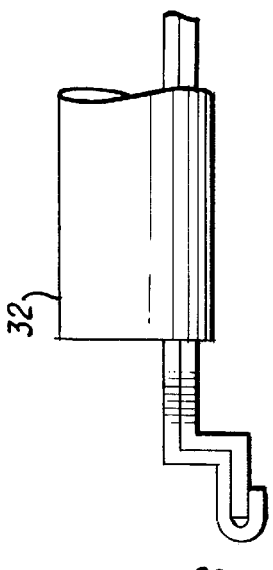 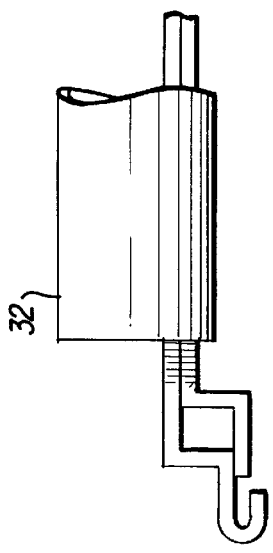 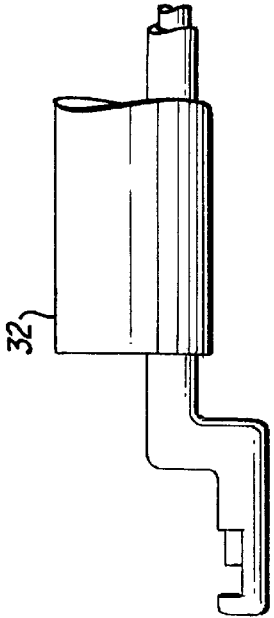
FIG. 4E  FIG. 4F  FIG. 4K
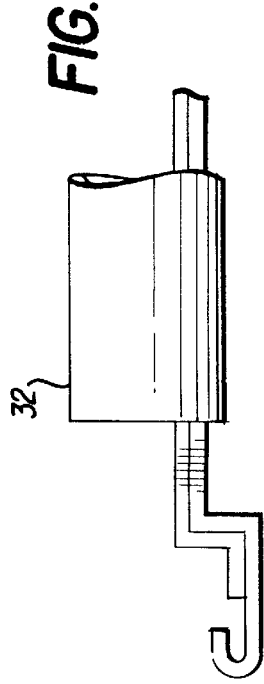 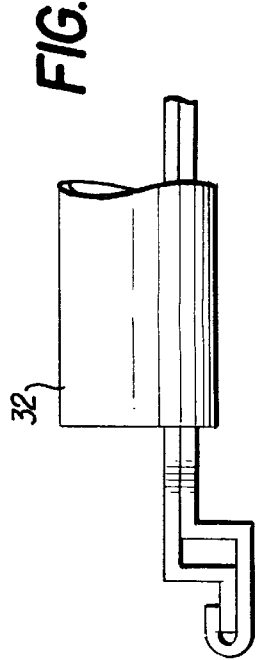 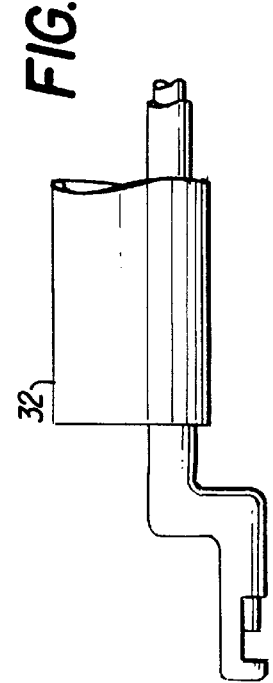
FIG. 4G  FIG. 4H  FIG. 4L

METHOD OF USING SURGICAL INSTRUMENT WITH ROTATABLY MOUNTED OFFSET END EFFECTOR

RELATED APPLICATION DATA

This application is a Div. of Ser. No. 08/847,252 filed on May. 1, 1997, now U.S. Pat. No. 6,080,180 and is related to applicant's applications Ser. No. 08/366,285 filed on Dec. 29, 1994, now U.S. Pat. No. 5,665,109, Ser. No. 08/377,723 filed on Jan. 25, 1995, now U.S. Pat. No. 5,643,745 Ser. No. 08/401,002 filed Mar. 9, 1995, now U.S. Pat. No. 5,695,505, Ser. No. 08/585,875 filed Jan. 16, 1996, now U.S. Pat. No. 5,810,853, and Ser. No. 08/758,648 filed Nov. 27, 1996, now U.S. Pat. No. 5,759,188, the disclosures of which are incorporated herein by reference. Also, this application is related to applicant's concurrently filed applications entitled "Surgical Instrument with Multiple Rotatably Mounted Offset End Effectors and Method of Using the Same", "Suturing Instrument with Rotatably Mounted Offset Needle Holder and Method of Using the Same", and "Suturing Instrument with Multiple Rotatably Mounted Offset Needle Holders and Method of Using the Same", the disclosures of which are also incorporated herein by reference.

BACKGROUND OF THE INVENTION

1. Field of the Invention

The present invention pertains to a methods and apparatus for endoscopic and open surgery and, more particularly, to various end effectors of a surgical device that are offset from an axis and methods of manipulating these end effectors.

2. Discussion of the Related Art

Various steps are accomplished in both open surgery and endoscopic surgery. Generally the multiple steps require various operating instruments. "Open surgery" refers to surgery wherein the surgeon gains access to the surgical site by a relatively large incision and "endoscopic surgery" refers to minimally invasive surgery wherein the surgeon gains access to the surgical site via one or more portals through which endoscopes are introduced to view the surgical site and through which instruments having "end effectors", such as forceps, cutters, needle holders, cauterizers, and the like, are introduced to the surgical site.

The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like into the anatomical cavity.

The various end effectors at the distal end of the instrument are manipulated by the surgeon using controls disposed at the proximal end of the instrument. Of course, it is desirable to move the end effectors through various paths, depending on the step being performed. Traditionally, this was accomplished by moving the entire end of the endoscopic instrument. However, recently it has been proposed to provide a plurality of end effectors on a single endoscopic instrument to minimize the number of puncture sites and thus reduce the risk and healing time associated with endoscopic surgery. See applicant's concurrently filed patent applications entitled "Suturing Instrument with Multiple Rotatably Mounted Offset End Effectors and Method of Using the Same" and "Surgical Instrument with Multiple Rotatably Mounted Offset Needle Holders and Method of Using the Same", the disclosures of which are incorporated herein by reference.

When a plurality of end effectors are incorporated into a single endoscopic device it is desirable to move the end effectors individually with respect to one another without necessarily moving the entire device. Also, even in single end effector devices, it is often desirable to move the end effector through a predetermined path, such as an arc or the like during an operative step, without repositioning the entire endoscopic device.

Of course, it is also generally desirable to minimize the size of each puncture site. Further, in order to permit operations on a wide range of tissue sizes, it is desirable to provide a wide range of relative movement between the end effectors. These objectives, minimal number/small size punctures and wide range of relative movement, are seemingly contradictory. Conventional devices have not achieved the above-noted objectives.

U.S. Pat. No. 5,582,617 discloses an endoscopic instrument having an end effector that can move from a position within the diameter of the barrel of the device to a position outside the diameter. However, this device must pivot about an axis that is transverse to the axis of the barrel and an axis that is coincident with the axis of the barrel and thus requires a complex movement and linkage to accomplish the disclosed functions. Accordingly, this device falls short of providing an end effector that can be utilized over a large working span for a wide range of applications.

SUMMARY OF THE INVENTION

Accordingly, it is a primary object of the present invention to overcome the above-mentioned disadvantages of the prior art and to improve surgical instruments and methods of surgery including endoscopic surgery.

It is also an object of the invention to provide an endoscopic device having a large working span and a small insertion diameter.

Yet another object of the present invention is to minimize the number of puncture sites required for performing operative steps on anatomical tissue in an endoscopic procedure by conducting multiple procedures through a single puncture site with an instrument that is operable to move an end effector through a predetermined path to operate on anatomical tissue.

The present invention is generally characterized in an instrument for operating on anatomical tissue including a barrel, a shaft extending through the barrel and an end effector mounted on the shaft. The end effector is offset from the longitudinal axis of the shaft by a connecting member to permit the end effector to move through a path that is outside of the diametrical dimension of the barrel. During insertion, the end effector can be positioned within a diametrical dimension of the surgical instrument either by rotating the shaft or by drawing the shaft and the end effector into the barrel in an axial manner.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 1 illustrates a first preferred embodiment of the invention;

FIGS. 2A and 2B illustrate the first preferred embodiment as viewed from a distal end;

FIG. 3 is a perspective view of the distal end of the first preferred embodiment;

FIG. 4A illustrates the driver removed from the barrel;

FIG. 4B illustrates the distal end of a modified driver;

FIG. 4C illustrates the distal end of a modified driver;

FIG. 4D illustrates the distal end of a modified driver;

FIG. 4E shows a distal end of the preferred embodiment with a modified jaws in the open position;

FIG. 4F shows a distal end of the preferred embodiment with a modified jaws in the closed position;

FIG. 4G shows a distal end of the preferred embodiment with another modified jaws in the closed position;

FIG. 4H shows a distal end of the preferred embodiment with another modified jaws in the open position;

FIG. 4K illustrates a distal end of the preferred embodiment with another modified jaws;

FIG. 4L illustrates a distal end of the preferred embodiment with another modified jaws;

FIGS. 6A and 6B illustrate a second preferred embodiment; and

DETAILED DESCRIPTION OF THE PREFERRED EMBODIMENTS

Figure 5A:
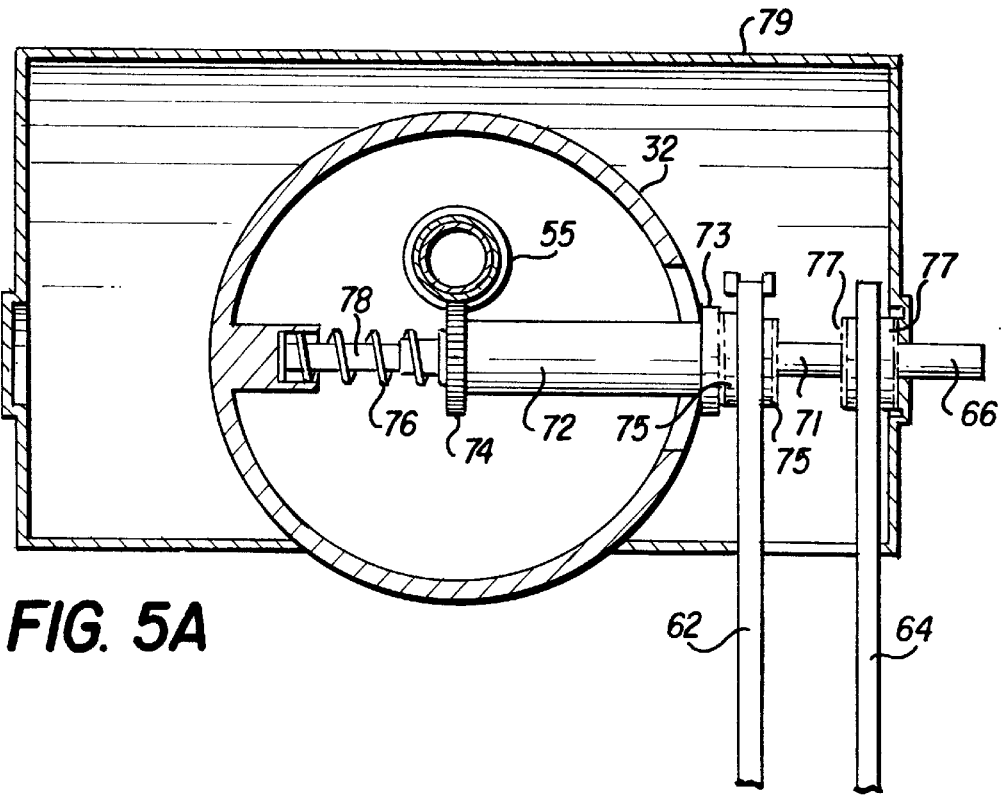
FIGS. 5A and 5B illustrate the inner mechanism of the proximal controls of the first preferred embodiment taken along line 5—5 of FIG. 2.

The surgical instrument of the present invention can be utilized to operate on any type of anatomical tissue in any type of anatomical cavity; and, accordingly, while the instrument is described hereinafter for use with a portal sleeve in endoscopic procedures, such as laparoscopy, the instrument can be used in open surgery and with catheters and other small and large diameter tubular or hollow, cylindrical members providing access to small cavities, such as veins and arteries, as well as large cavities, such as the abdomen.

An instrument according to a first preferred embodiment of the present invention is illustrated at 30 in FIG. 1 and includes cylindrical barrel, or outer shaft, 32 which has an elongated passage defined therein. Driver 40 includes a shaft which is received in barrel 32. The shaft is constituted of tubular inner member 44 disposed in tubular outer member 42, as illustrated in FIG. 4. However, the shaft can be a singular tubular member, a solid member or of any other appropriate configuration. Driver 40 also has arms 51A and 51B serving as connecting members between and end effector 50 and a distal end of inner member 44. Cam surfaces 52A and 52B are formed respectively on arms 51A and 51B. End effector 50 can be any appropriate type of end effector such as a needle holder, forceps, a clamp, a cauterizer, a clip applicator or the like. In this preferred embodiment, end effector 50 is forceps jaws comprising jaw members 50A and 50B disposed on arms 51A and 51B respectively. Arms 51A and 51B extend transversely, and preferably perpendicular, from the shaft. Also, as shown in FIG. 4, flanges 46 are formed on a proximal end of outer member 42 to fix collar 55 axially on outer member 42.

As shown in FIG. 1, barrel 32 is an elongated tubular member terminating distally at a distal end for being disposed within the body cavity of a patient and terminating proximally at a proximal end for being disposed externally of the patient. As shown in FIG. 3, barrel 32 includes a plurality of channels 38a–d extending longitudinally through barrel 32. The shaft of driver 40 is rotatably mounted in channel 38d. Barrel 32 can have additional channels for receiving one or more additional instruments to be introduced in the abdominal cavity or barrel 32 can have fewer channels. Aperture 70 is formed in arm 51A to communicate with an interior of inner member 44. This permits an additional channel be defined through inner member 44.

One or more light transmitting elements, such as a plurality of light transmitting fibers 39, extend longitudinally through barrel 32 as is required. However, the light transmitting fibers can be omitted and a void space can be defined between channels 38a–d by appropriate spacers or the like. Also, the light transmitting elements can be confined to one or more of operating channels 38a–d. Operating channels 38a–d are formed by thin wall, tubular sleeves extending longitudinally through barrel 32 with light transmitting fibers 39 being disposed in the space between the sleeves and barrel 32. Alternatively, channels 38a–d can be defined in barrel 32 without sleeves to further reduce the external diametric cross-sectional size of barrel 12. For instance, light transmitting fibers 39 can be rigidly arranged and secured in barrel 32 to define channels 38a–d, and the inner surface of barrel 32 can define peripheral or circumferential segments of one or more of channels 38a–d. Light transmitting fibers 39 are designed to transmit light from a proximal light source (not shown) to the distal end to provide illumination in the body cavity. Barrel 32 can have a light coupler at the proximal end thereof for connection to a light source in a known manner. Also, retractable cylindrical sheath 57 can be disposed over barrel 32 to shield and protect end effector 50 during insertion through a portal sleeve or the like and can be retracted proximally after insertion, as illustrated by the dotted line in FIG. 3. Any type of structure can be used to protect end effector 50.

Inner member 44 and outer member 42 are substantially disposed in channel 38d which is offset from an axial center of barrel 32 in this embodiment. Also, as noted above, a channel through inner member 44 communicates to the proximal end of the instrument through aperture 70 formed in arm 51A. This channel can be used for insertion of instruments, aspiration, irrigation, or the like.

FIG. 2A schematically illustrates the distal end of instrument 30 when driver 40 is rotated to place end effector 50 in the insertion, or parked, position. In this position, arms 51A and 51B and end effector 50 are contained within the diametrical dimension of barrel 32 as viewed from the distal end. Also, sheath 57 or another structure can be used when end effector 50 is in this position. This permits instrument 30 to be inserted through a standard portal sleeve having a sealing element. However, after the distal end of instrument 30 is inserted into an anatomical cavity, the shaft of driver 40 is rotated in either direction, to the position illustrated in FIG. 2B, for example. In this position end effector 50 is positioned outside of the diametrical diameter of barrel 32. The path of movement of end effector 50 is a relatively wide arcuate path as indicated by the arrows in FIGS. 2A and 2B. This facilitates manipulation of end effector 50 which can be a suturing device, forceps, stapler, clamp, or the like.

Control of end effector 50 can be accomplished by the surgeon by manipulating proximal controls 60. As illustrated in FIG. 1, proximal controls 60 of the preferred embodiment include scissor type handles 62 and 64, extending from housing 79, that can be pivoted towards one another to cause movement of end effector 50, in this embodiment jaw members 50A and 50B. Button 66 is provided proximate an axis of rotation of handles 62 and 64. Depressing button 66 disengages handles 62 and 64 from driver 40 and permits handles 62 and 64 to be rotated in concert about the axis of rotation as indicated by arrow A in FIG. 1. This allows the surgeon to orient handles 62 and 64 in a desired manner during surgery.

Figure 5B:
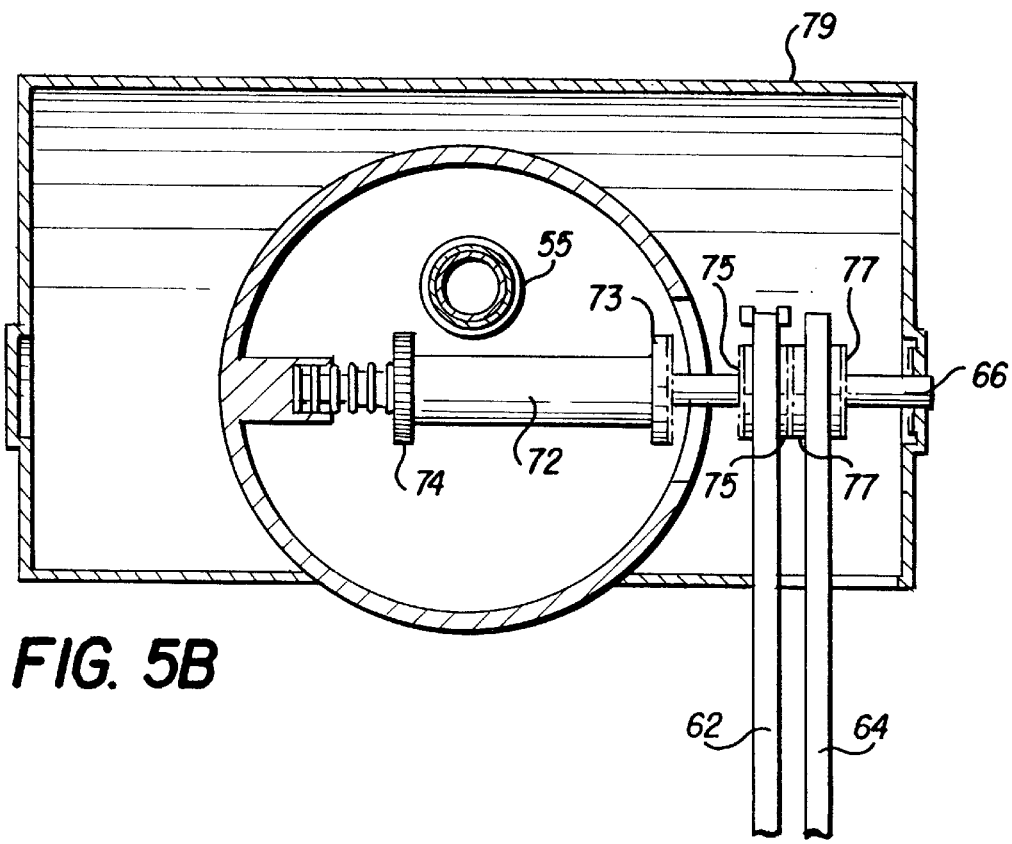

FIGS. 5A and 5B illustrate the internal mechanism coupling handles 62 and 64 to driver 40. Operating member 72 is rotatably disposed on shaft 71 and has gear portion 74 that is engaged with collar 55 on outer member 42 of driver 40. Operating member 72 is fixed axially on shaft 71 and has radially extending serrated teeth 73 formed on a side opposite gear portion 74. Handle 62 is also rotatably mounted on shaft 71 and is slidable relative to shaft 71. Handle 62 is fixed in axial position by projections formed on an inner surface of housing 79. Handle 62 has radially extending serrated teeth 75 on each side thereof at a top portion that is disposed around shaft 71. Shaft 71 is mounted on stem 78 and is normally biased to the right in FIG. 5A by spring 76 to press serrated teeth 73 into engagement with serrated teeth 75 thus fixing the relative position, of operating member 72 and handle 62. Handle 64 is rotatably mounted on shaft 71 and fixed axially on shaft 71. Serrated teeth 77 are formed on each side of handle 64 at a top portion that surrounds shaft 70 and serrated teeth 77 are normally biased by spring 76 into engagement with teeth formed on an inner surface of housing 79 to fix the position of handle 64 with respect to barrel 32. In this state handle 62 is coupled to outer member 42 of driver 40 and handle 64 is fixed in position. Pressing handle 62 towards handle 64 will cause outer member 42 to move over cam surfaces 52A and 52B (see FIG. 4A) to close jaws 50A and 50B.

When shaft 71 is pressed to the left, as illustrated in FIG. 5B, by depressing button 66, serrated teeth 77 engage serrated teeth 75 to fix the relative positions of handles 62 and 64 and serrated teeth 73 are disengaged from serrated teeth 75 to disengage handle 62 from driver 40. This permits the set of handles 62 and 64 to be rotated in concert to the desired orientation.

As noted above, cam surfaces 52A and 52B are formed on outer surfaces of arms 51A and 51B respectively. When handle 62 pressed towards handle 64, outer member 42 moves distally over cam surfaces 52A and 52B causing jaw members 50A and 50B to move toward one another to the closed position. Cam surfaces 52A and 52B can be formed by bent portions defined in legs 51A and 52B or by separate elements that are attached to, or formed on, legs 51A and 51B. Release of handles 62 and 64 causes jaw members 50A and 50B to return to the open position due to the resilient bias of arms 51A and 51B. Lock protrusions 63 and 65 are disposed on handles 62 and 64 respectively (see FIG. 1) and are serrated to interlock and allow the position of handles 62 and 64 to be maintained in a state corresponding to a desired position of jaw members 50A and 50B. Lock protrusions 63 and 65 can be pivoted to a position of which they will not interlock if desired. Additionally, handles 62 and 64 can be biased apart or outer member 42 can be biased distally or proximally, depending on desired operating characteristics.

A known optical observation device, such as an optical endoscope using fiber optics or a CCD device for transmitting an image from the distal end to the proximal end, can be inserted in channel 38b, for example, for permitting observation of the operation of the other elements. Channels 38a and 38c can be used as an operating channel for a suction device, an irrigation device, or any other appropriate instrument.

In use, instrument 30 is inserted into a body cavity using known techniques, while driver 40 is in the position illustrated in FIG. 2A. In this embodiment, end effector 50 is a forceps device having opposed grasping jaw members 50A and 50B and cutting portions 53 that can be used to selectively manipulate and cut tissue (See FIG. 3). However, end effector 50 can be any desired instrument, such as a cauterizing device, a clamp, a stapler, a clip applicator, or the like and can be used to pickup, spread, cut, coagulate, suture, apply clips to, or accomplish other operations on tissue.

In this embodiment, only a single puncture need be created to insert the entire instrument 30 which includes driver 40 and other operating channels. Also, during insertion, the entirety of driver 40, including end effector 50, is disposed in the protected position (sometimes referred to as a "parked" or "insertion" position herein) within the diametrical dimension of barrel 32.

By grasping proximal controls 60, the distal end of instrument 30 is guided to the operative site through a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. Visualization of the endoscopic procedure can be accomplished using a conventional endoscope incorporated into an unused one of the channels 38a–d, or separately positioned within the anatomical cavity through a second portal sleeve located at another puncture site.

At any point during the operative procedure, channels 38a or 38c can be used for irrigation or aspiration or can serve as a space for holding suture material or the like or as a portal for the introduction of other medical instruments such as, forceps, cutting members and endoscopes. Also, channel 38d can be used for irrigation, aspiration, or the like by utilizing the passage through the of driver 40. Knob 48 is coupled to the shaft, by a gear or the like and thus rotation of knob 48 will impart rotation to driver 40. Also, button 49 releases a locked state of knob 48 when pressed by the surgeon. Rotation of knob 48 thus causes end effector 50 to move through an arcuate path for manipulating tissue or performing other operations. Also, end effector 50 can be moved by rotating the entirety of instrument 30 about its longitudinal axis with driver 40 locked in position relative to barrel 32.

FIG. 4B illustrates a modified driver having pivoting jaw members 50A and 50B. FIG. 4D illustrates a modified driver having outer member 42 with a notch formed therein. Flexible inner member 44 can be moved proximally and distally with respect to outer member 44 to grasp tissue or other objects in the notch. These modified driver can be manipulated in a manner similar to the device described above.

FIG. 4E illustrates a distal end of instrument 30 having, a needle holders that includes hooked member 41 and sliding keeper 43 that can be moved distally and proximally with respect to hook member 41. A needle can be grasped when keeper 43 is advanced distally to the closed position illustrated in FIG. 4F. FIG. 4G illustrates a similar arrangement. However, hook member 41 opens outwardly. FIG. 4H shows the open position with keeper 43 withdrawn. FIG. 4K illustrates a distal end of instrument 30 having a needle holder that is configured as illustrated in FIG. 4D. FIG. 4L illustrates a similar configuration. However, in FIG. 4L, the notch in outer member 42 opens inwardly.

Figure 6B:
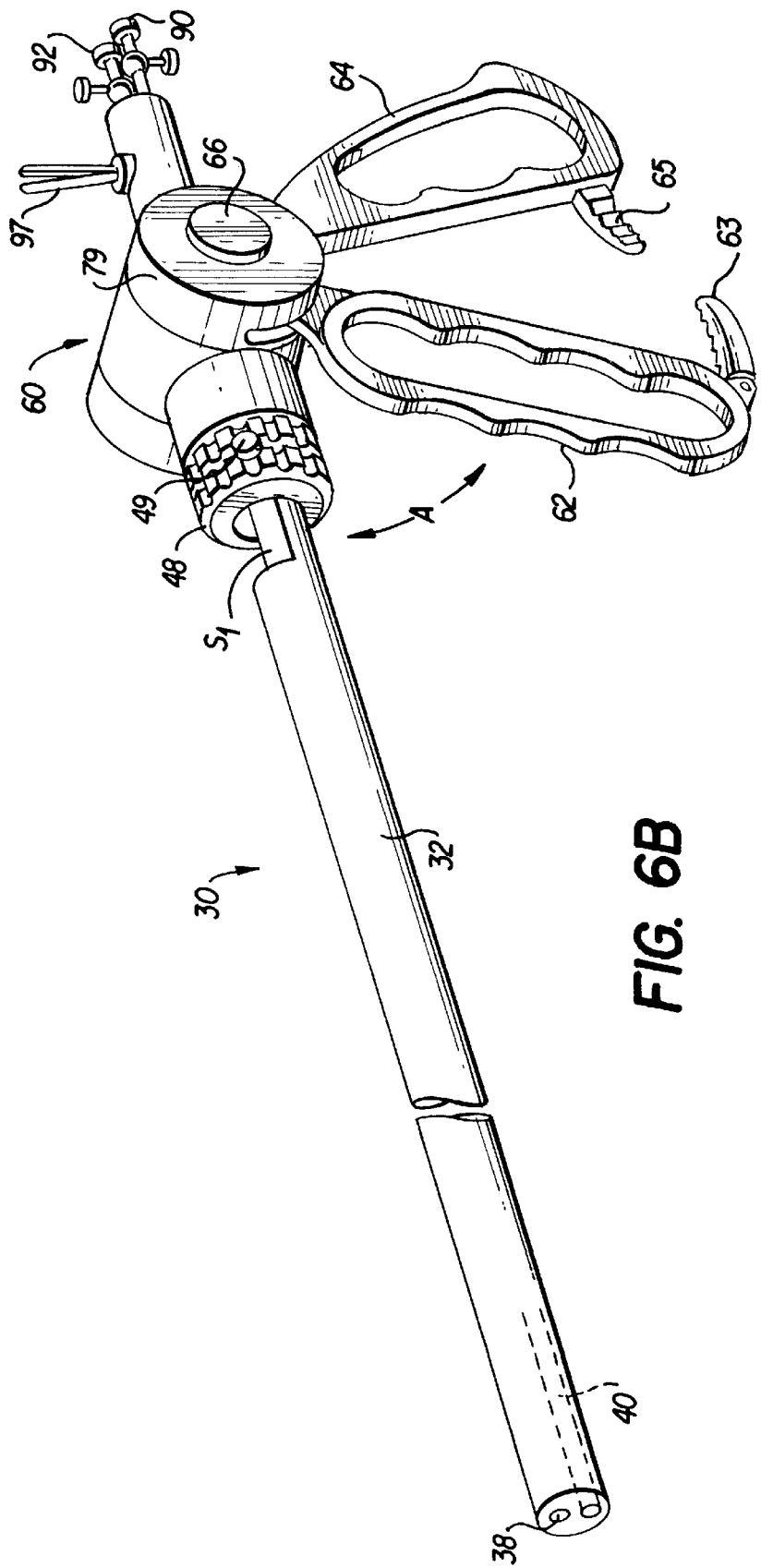

Arms 51A and 51B and end effector 50 of the first preferred embodiment are moved to and from the inserting position by rotating the shaft as described above. However, in a second preferred embodiment illustrated in FIGS. 6A and 6B, at least a portion of arms 51A and 51B are made of a resilient material or a shape memory material. As illustrated in FIGS. 6A and 6B, knob 48 is slidable in distal and proximal directions along slot S1 formed in barrel 32 to move driver 40 along the longitudinal axis of barrel 32.

Figure 7:
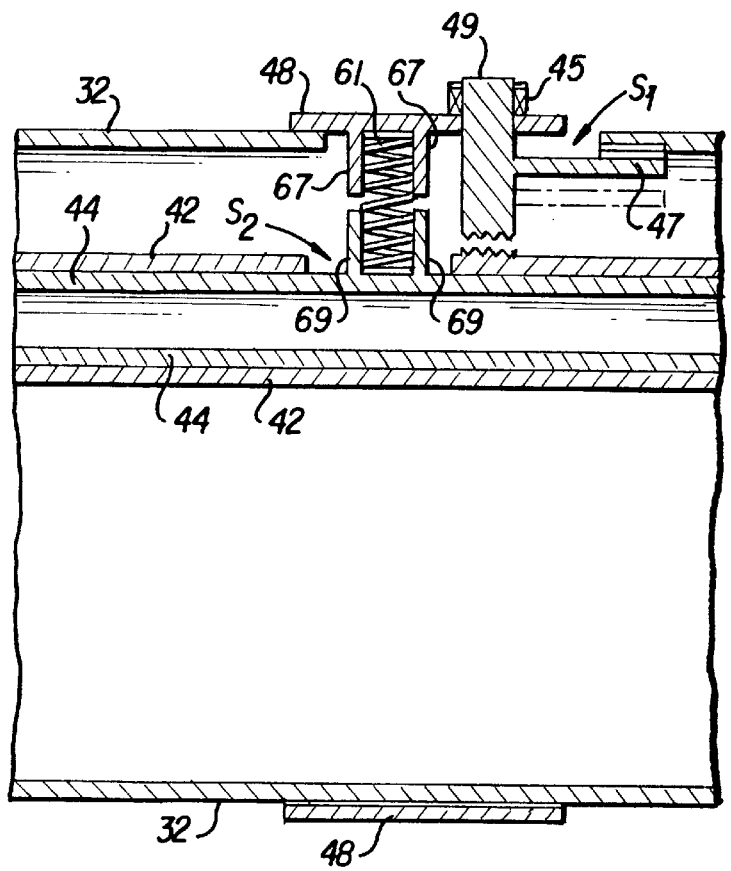
FIG. 7 is a sectional view of the rotating and sliding mechanism of the second preferred embodiment.

The internal mechanism coupling knob 48 to drive apparatus 40 is illustrated in FIG. 7. Slot S1 is formed in a portion of the circumference of barrel 32. Also, slot S2 is formed in a portion of the circumference of outer member 42 of driver 40. Gear 61 extends through slot S1 and slot S2 and is meshed with gear teeth formed on an inner surface of knob 48 and an outer surface of inner member 44 of driver 40. Projections 67 are formed on knob 48 and projections 69 are formed on inner member 44 to maintain gear 61 in a transverse position with respect to inner member 44 and to fix the relative linear position of knob 48 and inner member 44. Button 49 extends through a hole formed in knob 48 and has locking member 47 disposed on an end thereof. Button 49 is normally biased upward in FIG. 7 by spring 45 to cause locking member 47 to engage with a tread or teeth formed on the inner surface of barrel 32.

To slide driver 40 in the proximal direction, the surgeon presses button 49 downward in FIG. 7 until button 49 reaches the position shown by the dotted line in FIG. 7. This unlocks knob 48 by lowering locking member 47 and couples knob 48 to outer member 42 by pressing a lower portion of button 49 against outer member 42. Then, while holding button 49 in the depressed position, the surgeon slides knob 48 proximally, from the position illustrated in FIG. 6A to the position illustrated in FIG. 6B for example. Inner member 44 will move distally along with knob 48 because of projections 67 and 69 and gear 61 which couple knob 48 and inner member 42. Also, outer member 42 will move distally along with knob 48 and inner member 44 because button 49 is pressed against the outer surface of outer member 42. Of course, the frictional contact between button 49 and outer member 42 can be adjusted as needed by providing treads or the like on the contacting surfaces. Also, the dimensions and tolerances of all members can be adjusted to provide the described movement in a smooth and accurate manner. Of course, this embodiment can use the same controls for moving outer member 42 relative to inner member 44 as the first embodiment. In such a case. Button 66 should also be depressed when knob 48 is moved distally to permit outer member 42 to move freely.

Movement of knob 48 in the proximal direction will draw end effector 50 into barrel 32. Since at least portions of arms 51A and 51B are resilient or have shape memory characteristics, the bent portions thereof will straighten out to permit end effector 50 to be drawn at least in part into channel 38d of barrel 32, as illustrated by the dotted line in FIG. 6B. Insertion of instrument 30 can be accomplished easily while instrument 30 is in the state illustrated in FIG. 6B wherein end effector 50 is contained within the diametrical dimension of barrel 32. Of course, this embodiment can be utilized with a device having plural end effectors on plural shafts also. Also, knob 48 can be moved in the distal direction to place end effector 50 in an operative position, such as the position illustrated in FIG. 6A, in a similar manner.

Figure 8:
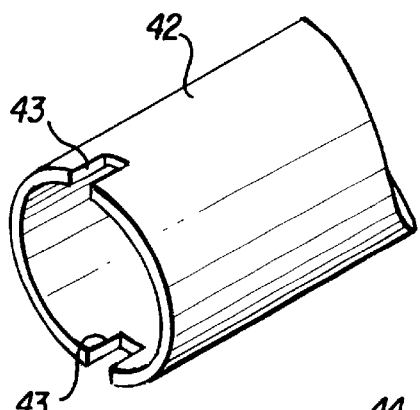
FIG. 8 is a distal end of a modified outer member.

With end effector 50 in an operative position, knob 48 can be rotated to rotate the shaft of driver 40 and move end effector 50 through an arcuate path, similar to the first embodiment illustrated in FIGS. 2A and 2B. To rotate the shaft, the surgeon depresses button 49 to the position illustrated by the dotted line to move locking member 47 away from barrel 32 and a lower portion of button 49 into contact with outer member 42. This unlocks knob 48 to permit rotation thereof. While holding button 49 in the depressed position, knob 48 is rotated. This causes gear 61 to rotate which causes inner member 44 to rotate. Outer member 42 can rotate at the same angular velocity as knob 48 and need not rotate along with inner member FIG. 4C illustrates the distal end of a modified driver 50 that is suitable for use with the second embodiment. This driver 50 is also constructed of resilient or shape memory material and has a shaft with an angled distal end. When driver 50 is drawn into barrel 42, driver 50 straightens out similar to the device illustrated in FIGS. 6A and 6B FIG. 8 illustrates a modified outer member having slots 43 in a distal end thereof.

Figure 9:
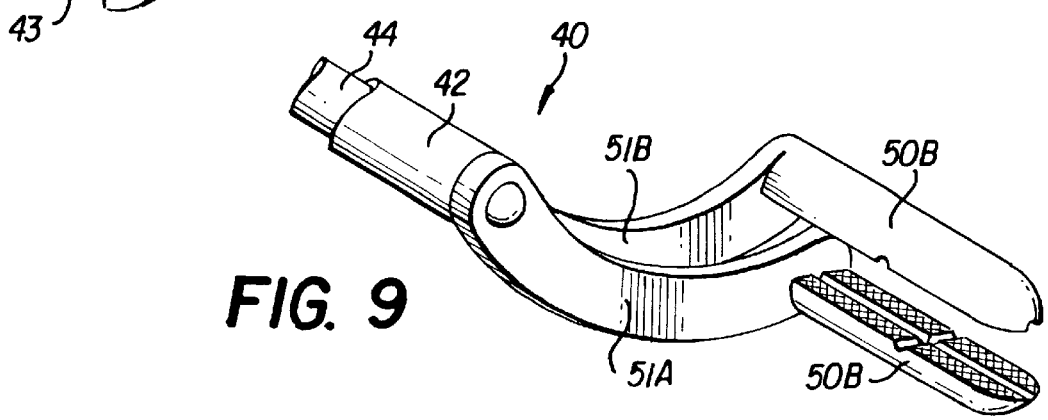
FIG. 9 illustrates another modified driver.

FIG. 9 illustrates the distal end of modified driver 40 in which arm member 51A is coupled to inner member 44 and arm member 51B is coupled to outer member 42. Relative rotation between inner member 42 and outer member 44 will cause jaw members 50A and 50B to open/close. Rotation in concert will move the end effector.

To permit one-handed operation of instrument 30 the motion of needle driver 40 can be accomplished automatically. In particular, handles 62 and 64 can be coupled to needle driver 40 in a manner which causes the desired rotation of the shaft of needle driver 40 and the opening and closing operation of the jaws necessary for a single operation, or multiple stitches, to be effected merely by squeezing and releasing handles 62 and 64 once or multiple times. The mechanism coupling handles 62 and 64 to needle driver 40 can be designed to accomplish any of the stitching functions disclosed above or any other appropriate motion. Such an automatic mechanism facilitates suturing by minimizing fatigue on the surgeon and reducing the possibility of operational errors. For example, the handle can be coupled to one or more end effectors to accomplish a desired procedure merely by squeezing and releasing the handles. Squeezing the handles can perform pickup and cutting, pickup and clipping, pickup and stapling, lysis of adhesion, or any other desired procedure or combination of procedures.

The mechanisms for moving the end effector in the preferred embodiments are merely exemplary of the types of mechanisms that can be used to perform these functions. For example, pistol grips or U-shaped members can be used to effect movement of the end effectors, as disclosed in the copending applications cited above, for example.

The present invention can be used to manipulate and cut tissue, when the end effector has forceps, jaws and a cutting member. Also, a clip applicator and a cutting member can be provided as the end effector, for example, to permit pickup and clipping, pickup and cutting, pickup and suturing or lysis of adhesion procedures. Any end effector can be used as a unipolar or bipolar cautery electrode by being coupled to an electric power source by connector 97. Further, the entire end effector can be used to push or separate tissue regardless of the end effector configuration.

The components of the present invention can be made of any suitable, medical grade materials to permit sterilization for reuse or disposal for single patient use. The components can be made of multiple parts of various configurations and materials to reduce cost. The invention can have various valves, stop cocks and seals therein to control the flow of fluid and medical devices through the suturing instrument. Also, the features of the disclosed embodiments can be combined.

Inasmuch as the present invention is, subject to many variations, modifications and changes in detail, it is intended that all subject matter discussed above or shown in the accompanying drawings be interpreted as illustrative only and not be construed as limiting the scope of the invention which is defined by the appended claims.

What is claimed is:

1. A method of effecting a surgical procedure on anatomical tissue, said method comprising the steps of:

providing an endoscopic device having a barrel with a distal end and a proximal end and a longitudinal axis, a handle coupled to the proximal end of the barrel, a driver having a distal end and extending through at least a portion of the barrel along a second axis radially offset from and substantially parallel to the longitudinal axis of the barrel, an end effector connected to the distal end of the driver, the end effector including two relatively movable members operable by said handle and disposed along a third axis radially offset from the second axis;

introducing the endoscopic device into an area proximate the anatomical tissue;

rotating the driver relative to the barrel about the second axis to move the movable members of the end effector between a first position in which the movable members are contained within a diametrical dimension of said barrel, and a second position in which at least a portion of the movable members of the end effector extend beyond the diametrical dimension of said barrel; and operating the handle to move the members of the end effector relative to one another to perform at least part of the surgical procedure.

2. The method of claim 1, wherein said introducing step includes the step of retracting the end effector into the distal end of the barrel with the end effector in the first position.

3. The method of claim 1, wherein the driver comprises a first tubular member disposed coaxially within a second tubular member, said rotating step comprising rotating the first and second tubular members relative to one another.

4. The method of claim 3, including the step of inserting an instrument through the first tubular member to the area proximate the anatomical tissue.

5. The method of claim 3 wherein the handle comprises a pair of relatively pivotable handles, the step of operating the handle comprising pivoting the handles relatively toward and away from one another to move the tubular members axially relative to one another.

6. The method of claim 1, including a knob mounted concentrically on the barrel and coupled to the driver for rotating the driver, said rotating step comprising rotating the knob about the longitudinal axis.

7. A method of effecting a surgical procedure on anatomical tissue, said method comprising the steps of:

providing an endoscopic device having a barrel with a distal end and a proximal end and a longitudinal axis, a handle coupled to the proximal end of the barrel, a driver having a distal end and extending through at least a portion of the barrel along a second axis radially offset from and substantially parallel to the longitudinal axis of the barrel, an end effector connected to the distal end of the driver, the end effector operable by said handle and including a connecting member extending transversely from the distal end of the driver and two relatively movable members coupled to the connecting member and disposed along a third axis radially offset from and substantially parallel to the second axis;

introducing the endoscopic device into an area proximate the anatomical tissue;

rotating the driver relative to the barrel about the second axis to move the end effector between a first position in which the movable members and the connecting member are contained within a diametrical dimension of said barrel, and a second position in which the movable members and at least a portion of the connecting member extend beyond the diametrical dimension of said barrel; and operating the handle to move the driver axially and the movable members of the end effector relative to one another to perform at least part of the surgical procedure.

* * * * *